US006846845B2

(12) United States Patent
Takahashi et al.

(10) Patent No.: US 6,846,845 B2
(45) Date of Patent: Jan. 25, 2005

(54) HEAT SHOCK PROTEIN INDUCER

(75) Inventors: Naohiko Takahashi, c/o Oita Medical Univeristy, 1-1 Idaigaoka, Hasama, Oita-gun, Oita (JP); Tatsuhiko Ooie, c/o Oita Medical University, 1-1 Idaigaoka, Hasama, Oita-gun, Oita (JP); Toshiie Sakata, c/o Oita Medical University, 1-1 Idaigaoka, Hasama, Oita-gun, Oita (JP); Kunitoshi Yamanaka, Oita (JP); Tomoko Nawata, Oita (JP); Masaya Arikawa, Oita (JP); Masahide Hara, Oita (JP); Tetsunori Saikawa, Oita (JP); Tatsuo Shimada, Oita (JP); Hironobu Yoshimatsu, Oita (JP)

(73) Assignees: Naohiko Takahashi, Oita (JP); Tatsuhiko Ooie, Oita (JP); Toshiie Sakata, Oita (JP); Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/230,361

(22) Filed: Aug. 29, 2002

(65) Prior Publication Data

US 2003/0134907 A1 Jul. 17, 2003

(30) Foreign Application Priority Data

Jan. 9, 2002 (JP) ......................................... 2002-002835

(51) Int. Cl.⁷ .............................................. A61K 31/12
(52) U.S. Cl. ...................................................... 514/675
(58) Field of Search ......................................... 514/675

(56) References Cited

U.S. PATENT DOCUMENTS 4,169,157 A     9/1979  Kijima et al.

FOREIGN PATENT DOCUMENTS

JP          53-145922          12/1978

OTHER PUBLICATIONS

Benjamin , I.J., and McMillan, D.R., "Stress (Heat Shock) Proteins Molecular Chaperones in Cardiovascular Biology and Disease,", *Circ. Res.* 83:. 117–132, Williams & Wilkens (1998).

Hutter, M.M. et al., "Heat–Shock Protein Induction in Rat Hearts: A Direct Correlation Between the Amount of Heat–Shock Protein Induced and the Degree of Myocardial Protection," *Circulation* 89: 355–360; American Heart Association (1994).

Malaoyan, A. et al., "Heart acclimation increases the basal HSP72 level and alters its production dymanics during heat stress," *Am. J. Physical.* 276:R1506–R1515. American Physiological Society (1999).

Maulik N. et al., "Drug–Induced Heat–Shock Preconditioning Improves Postischemic Ventricular Recovery After Cardiopulmonary Bypass," *Circulation* 92 (*Supplement II*):II–381–II3–88, American Heart Association (1995).

Mestril, R. et al., "Expression of Inducible Stress Protein 70 in Rat Heart Myogenic Cells Confers Protection against Stimulated Ischemia–induced Injury," *J. Clin. Invest.* 93:759–767, American Society for Clinical Investigation (1994).

Morris, S.D. et al., "Specific Induction of the 70–kD Heat Stress Proteins by the Tyrosine Kinase Inhibitor Herbimycin–A Protects Rats Neonatal Cardiomyocytes," *J. Clin. Invest.* 97:706–712, American Society for Clinical Investigation (1996).

Ooie, T. et al., "Single Oral Dose of Geranylgeranylacetone Induces Heat–Shock Protein 72 and Renders Protection Against Ischemia/Reperfusion Injury in Rat Heart," *Circulation* 104:1837,1843, American Heart Association (Oct. 2001).

Saikawa T. et al., "Oral geranylgeranylacetone induces heat shock protein and produces protection against ischaemia/reperfusion injury in rat heart," *Eur. Heart J.* 22:367, abstract No. 1936, W.B. Saunders (Sep. 2001).

Sun, L. et al., "Activation of HSF and selective increase in heat–shock proteins by acute dexamethasone treatment," *Am. J. Physiol. Heart Circ. Physiol.* 278: H1091–H1097, American Physiological Society (2000).

Xu Q, et al., "Nitric Oxide Induces Heart–shock Protein 70 Expression in Vascular Smooth Muscle Cells Via Activation of Heat Shock Factor 1," *J. Clin. Invest.* 100:1089–1097, American Society for Clinical Investigation (1997).

Yoshida, K. et al., "Translocation of protein kinese C–αδand ε isoforms in ischemic rat heart," *Biochem. Biophys. Acta* 1317:36–44, Elesvier Publishing Company (1996).

Dialog File 351, Accession No. 2057765, Derwent WPI English language abstract for JP53–145922 (Document AL1)—no date provided.

Bradford, Marion M., "A Rapid and Sensitive Method for the Quantitation of Microgram Quantities of Protein Utilizing the Principle of Protein–Dye Binding," *Anal. Biochem.* 72:248–254, Academic Press, Inc. 248–254 (1976).

Patent Abstracts of Japan—JP Patent Appl. Publication No. 53–145922 (Appl. Published Dec. 19, 1978); Japanese Patent Office.

*Primary Examiner*—Raymond J. Henley, III
(74) *Attorney, Agent, or Firm*—Sterne, Kessler, Goldstein & Fox P.L.L.C.

(57) ABSTRACT

A heat shock protein inducer is provided for purposes of preventing or treating ischemic disease or ischemia/reperfusion injury. This heat shock protein inducer has geranylgeranylacetone as an active ingredient and induces heat shock proteins in the heart.

6 Claims, 12 Drawing Sheets

FIG. 3
(A)
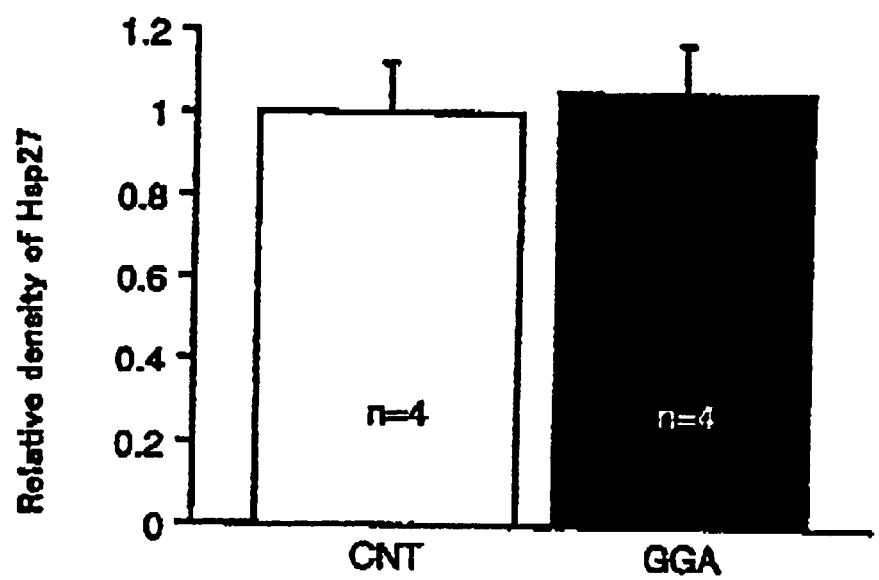
(B)
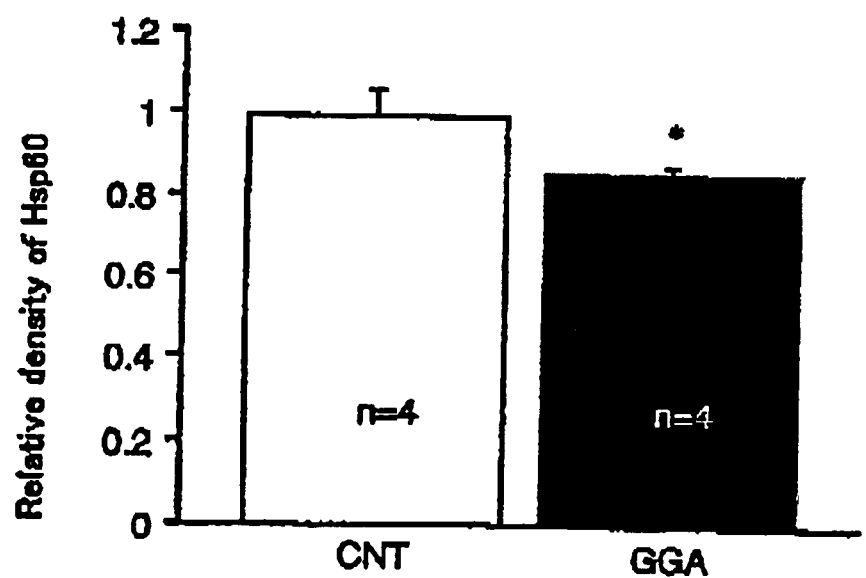

F I G. 4
(A)
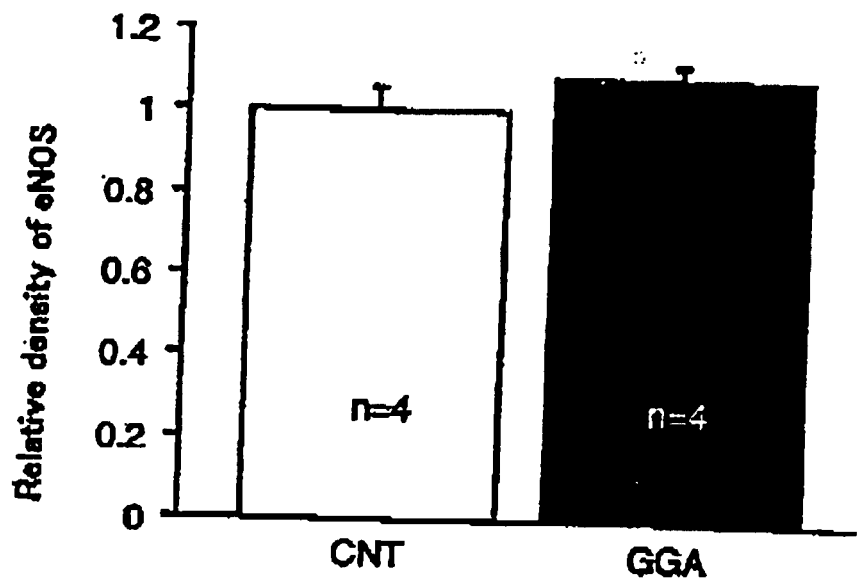
(B)
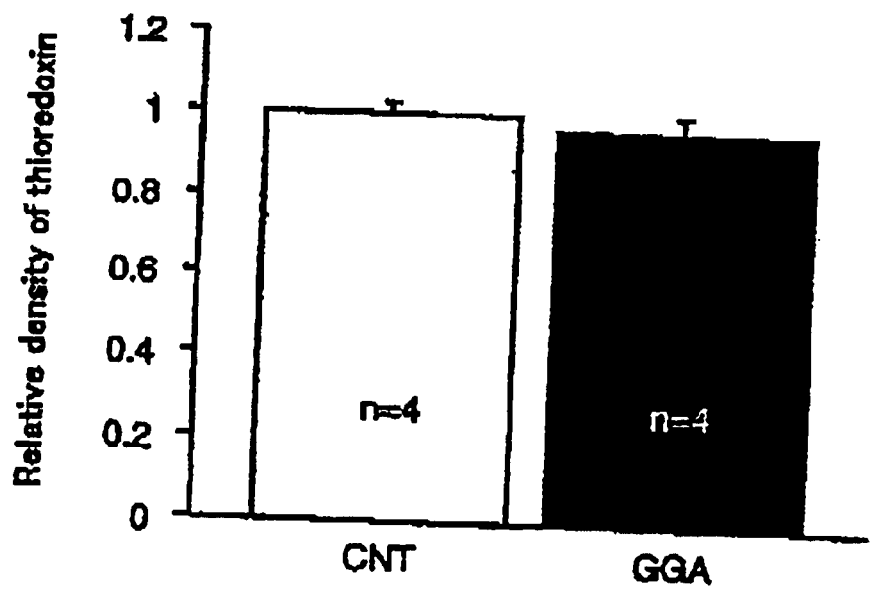

F I G. 6
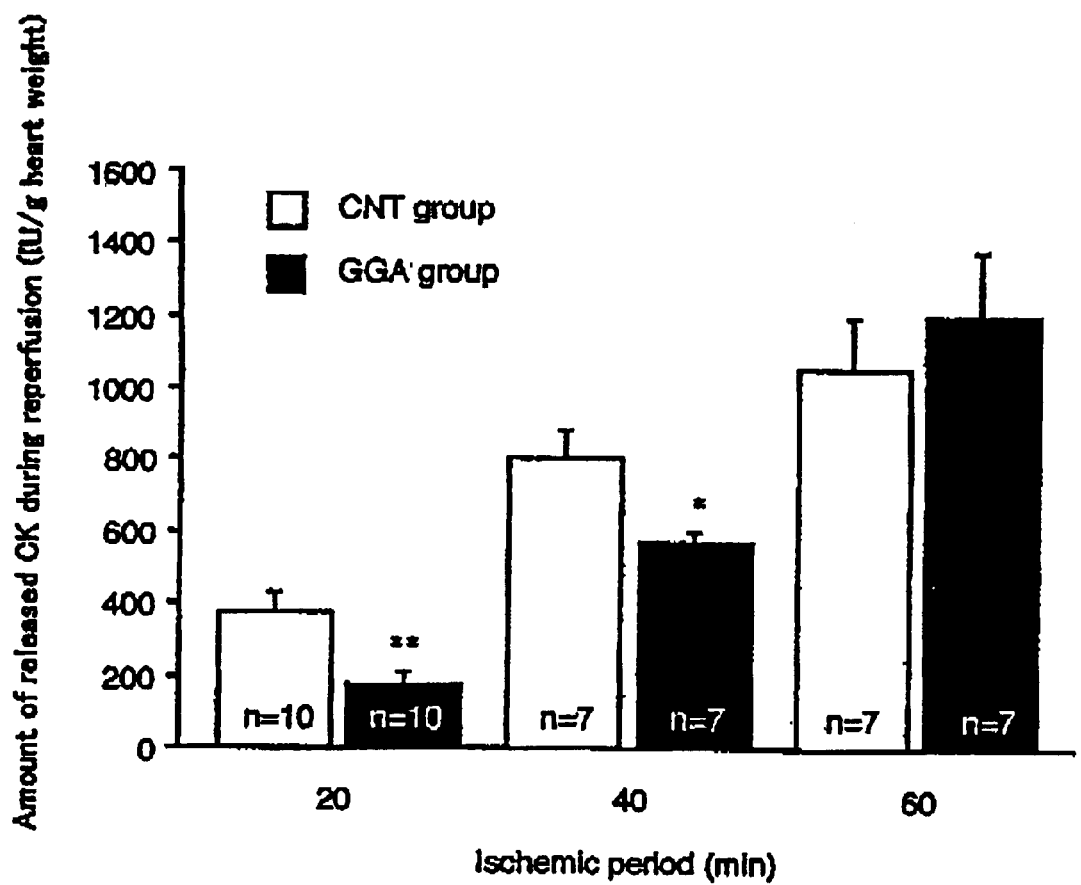

F I G. 12
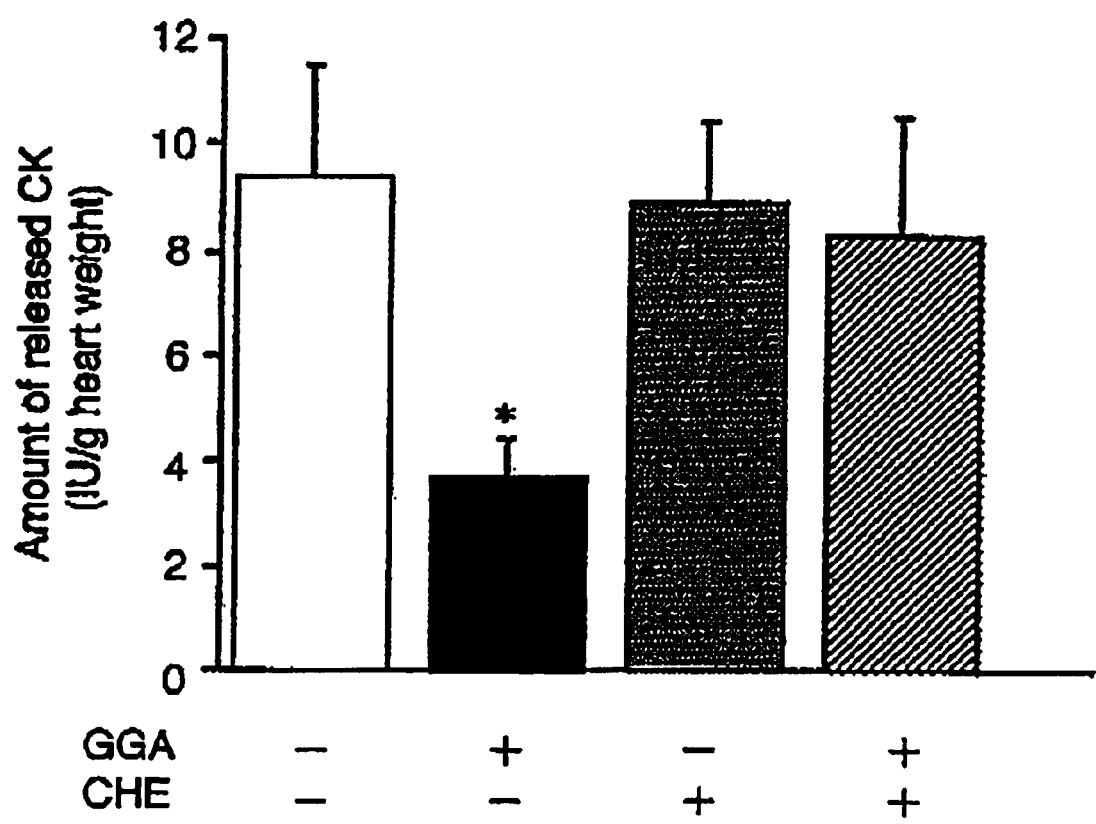

HEAT SHOCK PROTEIN INDUCER

CROSS-REFERENCE TO RELATED APPLICATIONS

This application claims benefit under 35 U.S.C. § 119(a)–(d) of Japanese Patent No. 2002-002835, filed Jan. 9, 2002, herein fully incorporated by reference.

BACKGROUND OF THE INVENTION

1. Field of the Invention

The present invention relates to a heat shock protein inducer, and more particularly to a heat shock protein inducer which is useful in preventing and treating damage to the myocardial cells from ischemia and perfusion.

2. Related Art

Ischemic disease (coronary heart disease) is caused by narrowing of the coronary artery. For example, in angina pectoris narrowing of the coronary artery leads to decreased blood flow volume, depriving the cardiac muscle of oxygen (ischemia) and depressing cardiac function. If this constriction (obstruction) of the coronary artery progresses, the result is myocardial infarction and necrosis of the heart muscle, and if necrosis is sufficiently widespread the heart ceases to function as a pump and death results.

When the obstructed coronary artery is reperfused in an effort to rescue cases of myocardial infarction, damage to the myocardial cells often results and has been known to cause myocardial failure (ischemia/reperfusion injury).

Heat shock proteins (abbreviated hereunder as "HSP") have been reported to have a cardioprotective function which alleviates ischemia/reperfusion injury. Namely, it has been reported that when myocardial cells are subjected to thermal stress or oxidation stress, heat shock proteins are expressed which confer ischemia resistance to the myocardial cells. Heat shock proteins are a family of endogenous protective proteins which are generated by various kinds of stress, such as heat shock (hyperthermia) or oxidation stress (hypoxia, hydrogen peroxide) (Bejamin IJ, McMillan D R. Stress (heat shock) proteins molecular chaperones in cardiovascular biology and disease. Circ Res 1998; 83:117–132).

For example, it has been reported that whole-body hyperthermia 24 hours before the onset of ischemic disease is protective against ischemia/reperfusion injury and is associated with proportional induction of shock protein (HSP70) expression (Hutter M M, Sieveres R E, Barbosa V et al. Heat-shock protein induction in rat hearts: a direct correlation between the amount of heat-shock protein induced and the degree of myocardial infarction. Circulation 1994; 89:355–360).

It has also been shown that ischemia resistance is high in myogenic cells and transgenic rats in which HSP70 is overexpressed (Mestril R, Chi SH, Sayen M R et al. Expression of inducible stress protein in rat heart myogenic cells confers protection against simulated ischemia-induced injury. J Clin Invest 1994: 93:759–767).

With this in view, therapies have been attempted involving the administration of heat shock protein inducers, which promote (induce) the expression of heat shock proteins in the heart (Morris S D, Cumming D E, Latchman D S et al. Specific induction of the 70-kD heat stress proteins by the tyrosine kinase inhibitor Herbimycin-A protects rat neonatal cardiomyocytes. J Clin Invest 1996; 97:706–712; Maulik N, Engelman R M, Wei Z et al. Drug-induced heat shock preconditioning improves postischemic ventricular recovery after cardiopulmonary bypass. Circulation 1995; 92(Suppl): 11381–11388; Sun L, Chang J, Kirchhoff S R et al, Activation of HSF and selective increase in heat-shock proteins by acute dexamethasone treatment. Am J Physiol 2000; 278:HI090–HI097).

The fact remains, however, that no heat shock protein inducer has yet been offered which does a good job of inducing heat shock proteins in the heart and presents no problems in terms of toxicity or side-effects.

SUMMARY OF THE INVENTION

Consequently, it is an object of the present invention to provide a heat shock protein inducer which is useful in the treatment of ischemic disease and of ischemic/reperfusion injury in particular and which has extremely little toxicity and few side-effects.

After painstaking research, the present invention was perfected as a result of the discovery that heat shock proteins can be effectively induced in the heart through administration of a heat shock protein inducer containing as an active ingredient the acyclic polyisoprenoid geranylgeranylacetone, and after further investigation based on this discovery.

The invention also includes a method of preventing or treating ischemic disease comprising the administration of a heat shock protein inducer containing acyclic polyisoprenoid geranylgeranylacetone to a patient in need thereof.

The invention further includes a method of preventing or treating ischemia/reperfusion injury comprising the administration of a heat shock protein inducer containing acyclic polyisoprenoid geranylgeranylacetone to a patient in need thereof and wherein the heat shock protein inducer is administered orally.

BRIEF DESCRIPTION OF THE FIGURES

FIG. 3 is a graph showing measurement results for (A) HSP27 induction and (B) HSP60 induction in the heart following oral administration of GGA or the vehicle;

FIG. 4 is a graph showing measurement results for induction of (A) NOS and (B) thioredoxin in the heart following oral administration of GGA and the vehicle;

FIG. 6 is a graph showing creatine kinase (CK) released during reperfusion.

FIG. 12 is a graph showing the amount of released creatine kinase (CK) relative to ventricular weight during the 30-min reperfusion period. Data are mean±SEM. *p<0.05 vs. control group.

DETAILED DESCRIPTION OF THE INVENTION

Figure 1:
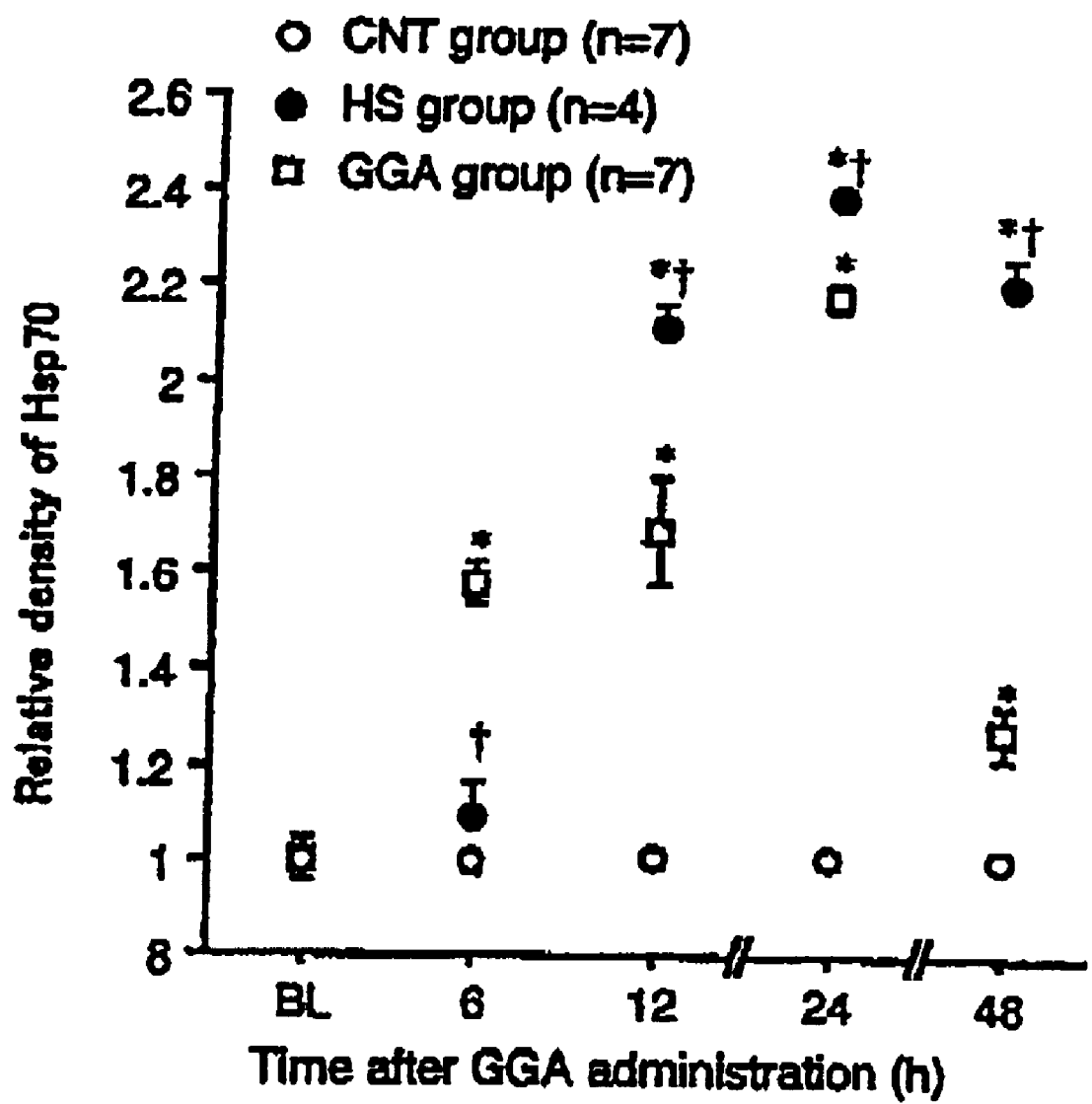
FIG. 1 is a graph showing changes over time in HSP70 induction in the heart following oral administration of GGA or the vehicle.

The heat shock protein inducer of the present invention features geranylgeranylacetone (GGA) as its active ingredient, and induces heat shock proteins in the heart.

Geranylgeranylacetone (GGA) is 6, 10, 14, 18-tetramethyl-5, 9, 13, 17-nonadecatetraen-2-one. More specifically, it is preferable to use (5E, 9E, 13E) 6, 10, 14, 18-tetramethyl-5, 9, 13, 17-nonadecatetraen-2-one, (5Z, 9E, 13E) 6, 10, 14, 18-tetramethyl-5, 9, 13, 17-nonadecatetraen-2-one, or a mixture of (5E, 9E, 13E) 6, 10, 14, 18-tetramethyl-5, 9, 13, 17-nonadecatetraen-2-one and (5Z, 9E, 13E) 6, 10, 14, 18-tetramethyl-5, 9, 13, 17-nonadecatetraen-2-one in an arbitrary ratio. It is more preferable to use a mixture of (5E, 9E, 13E) 6, 10, 14, 18-tetramethyl-5, 9, 13, 17-nonadecatetraen-2-one and (5Z, 9E, 13E) 6, 10, 14, 18-tetramethyl-5, 9, 13, 17-nonadecatetraen-2-one in 3:2 ratio. GGA is a well-known chemical which can be obtained as a reagent or industrial raw material and is synthesized according to well-known methods of synthesis such as those disclosed in Japanese Patent Application Laid-open No. 53-145922. GGA exists as 8 different geometrical isomers, of which any one or a mixture of two or more may be used in the present invention without any particular restrictions.

In the present invention, the term "heat shock protein" includes not only proteins expressed due to heat shock (thermal stress), but also proteins expressed due to oxidation stress.

Induction of heat shock protein in the heart is thought to be controlled by a specific heat shock factor (HSF). It is thought that HSF is present in the cytoplasm as an inactive form of monomer which is temporarily activated when exposed to heat stress or oxidation stress, and is involved in the induction of heat shock proteins. Although the mechanism of action of the present invention is unclear, it is surmised that upon administration of the heat shock protein inducer of the present invention the GGA which is its active ingredient acts in some way upon HSF, resulting in the induction of heat shock proteins in the heart.

The fact that the heat shock protein induced by the heat shock protein inducer of the present invention is HSP70 is desirable from the standpoint of increasing resistance to ischemic disease. In the present invention, the term "HSP70" is synonymous with "HSP72" or "HSP70".

Namely, the heat shock protein inducer of the present invention contains GGA as its active ingredient and is particularly useful in inducing (promoting the expression of) HSP70.

The heat shock protein inducer of the present invention may be administered either orally or parenterally in a suitable form to mammals (such as humans, dogs, cats, mice, rats, rabbits, cows, pigs, monkeys or the like). Oral administration is particularly desirable from the standpoint of promoting induction of heat shock proteins, as well as ease of administration.

The dosage (amount of active ingredient) of the heat shock protein inducer of the present invention is determined according to the animal to which it is being administered and the disease, symptoms, age, weight, complications, administration time, administration method, formulation and the like, but for example when used for treatment of myocardial infarction or angina in adult humans, a dose of 100 mg–3.0 g should be administered 1–3 times a day. Administration of 150 mg–1.5 g 1–3 times a day is preferred.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

For purposes of oral administration formulation should be in either solid or liquid form, such as tablets, coated tablets, pills, grains, granules, powder, capsules, syrup, emulsion, suspension or injection.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

When the formulation is a tablet or the like, it may be manufactured using vehicles ordinarily used in the pharmaceutical field (such as lactose, saccharose, starch, mannitol or the like), and when it is an injection or the like, it may be manufactured with emulsification or solubilization using soy lecithin or other natural surfactants or polysorbate or polyoxyethyne hydrogenated castor oil or other synthetic surfactants or the like.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The heat shock inducer of the present invention may also be administered as a medicinal composition containing any necessary antioxidants, binders (such as starch alpha amylase, gum arabic, carboxymethylcellulose, polyvinylpyrrolidone, hydroxypropyl cellulose and the like), disintegrators (such as calcium carbonate, carboxymethylcellulose calcium and the like), lubricants (such as talc, magnesium stearate, polyethylene glycol 6000 and the like), colorants, flavorings and the like.

Injectable preparations, drops, suppositories and preparations for external use are desirable formulations for parenteral administration. Because it induces heat shock proteins in the heart, the heat shock protein inducer of the present invention is especially useful for preventing or treating ischemic disease (angina, myocardial infarction and the like). Also, because it induces heat shock proteins in the heart, the heat shock protein inducer of the present invention is especially useful for preventing or treating ischemia/reperfusion injury following coronary bypass or other cardiac surgeries or following cardiac transplant. The compounds of the present invention find additional use in the treatment of restenosis following an injury such as balloon angioplasty, atherectomy, and arterial stent placement. The compounds of the invention can protect the myocardium from, hypoxia, cell toxins, and other noxious stimuli and thus are useful for the treatment of myocardial infarction and in other conditions resulting from vascular blockage. The compounds of the invention can be used in a method of preconditioning of cardiac myocytes in in vitro studies using cultured heart myocytes and in simulated ischemia studies.

Moreover, the medicament of the present invention is characterized by having geranylgeranylacetone as its active ingredient, and by being used for preventing or treating ischemic disease or ischemia/reperfusion injury. The medicament of the present invention may be a medicament composition containing vehicles, diluents and the like ordinarily used in the pharmaceutical field as mentioned above, or may consist of GGA alone. Because the medicament of the present invention contains GGA as an active ingredient, it can be effectively used for preventing or treating ischemic disease or ischemia/reperfusion injury.

And, the medicament of the present invention has geranylgeranylacetone as an active ingredient which activates translocation PKC δ, leading to the phosphorylation and/or translocation of the heat shock factor 1 (HSF1), and thus promote the expression of heat shock proteins 70 (HSP70) in the heart.

EXAMPLES

Examples provided are intended to assist in a further understanding of the invention. Particular materials employed, species and conditions are intended to be further illustrative of the invention and not limiting of the reasonable scope thereof.

All experimental procedures were in accordance with the guidelines of the Physiological Society of Oita Medical University, Japan, for the care and use of laboratory animals.

Example 1

Materials

Monoclonal IgG antibody cross-reactive to HSP70, HSP60 and HSP27 antibodies was purchased from Stressgen Biotechnologies Corporation (Sydney, Canada). Primary antibodies of nitric oxide synthase (NOS) or in other words inducible NOS (iNOS), endothelial NOS (eNOS) and neuronal NOS (nNOS) were purchased from Transduction Laboratories (Lexington, Ky.). The primary antibody of thioredoxin was kindly provided by Professor Yodoi of Kyoto University.

Horseradish peroxidase-linked F(ab')2 fragment from sheep anti-mouse immunoglobulin and reagents for Western blot detection by enhanced chemiluminescence (ECL) were purchased from Amersham Pharmacia (Arlington, Ill.). Bradford protein assay kits were purchased from Bio-Rad Laboratories (Richmond, Calif.).

An emulsification of gum arabic by itself was used as the vehicle for administration to the control rats.

Measuring the Induced Amount of Heat Shock Protein

Male Sprague-Dawley rats (220–250 g) were anesthetized with pentobarbital (20 mg/kg, i.p.). They were subjected to whole-body hyperthermia by soaking for 10 minutes in a bath in which the water temperature was maintained at 43° C. (Heat Stress Group), with their heads on pillows to avoid aspiration of water. rectal temperatures were measured as body temperatures rose throughout the whole-body hyperthermia.

An emulsion of 100% by weight of geranylgeranylacetone (GGA) with 5% by weight of gum arabic and 0.008% by weight of tocopherol was given orally to the rats described above. The oral dosages were 50 mg/kg, 100 mg/kg, 200 mg/kg and 400 mg/kg (GGA groups). No particular abnormalities (side-effects) were observed in the rats during administration of this GGA. The vehicle was administered orally to the Control Group.

To examine the time-dependent expression of HSP70, rats were killed by deep anesthesia with pentobarbital (50 mg/kg, i.v.) 6, 12, 24 and 48 hours after administration of the GGA or vehicle or 6, 12, 24 and 48 hours after heat stress.

Next, the hearts were removed from the killed rats and frozen in liquid nitrogen.

Western blotting was then performed (Maloyan A, Palmon A, Horowitz M. Heat acclimation increases the basal HSP70 level and alters its production dynamics during heat stress. Am J Physiol 1999; 276:R1506–R1515). The frozen hearts were homogenized with SDS (sodium dodecyl sulfate) buffer, centrifuged and boiled.

The total protein concentration of the myocardium was quantified by the Bradford method (Bradford M M. A rapid and sensitive method for quantitation of microgram quantities of protein utilizing the principle of protein-dye binding. Anal Biochem 1976; 72:248–254). The prepared hearts were then diluted in electrolyte buffer. Total protein in each heart was subjected to electrophoresis on 8.5% SDS-Polyacrylamide gel (SDS-PAGE), and transferred to a PVDF (polyvinylidene fluoride) membrane. After blocking with 0.5% nonfat milk, the PVDF membranes were incubated with antibodies. The proteins were detected by exposing the ECL cells with Hyperfilm (Amersham Pharmacia, Buckinghamshire, UK). Based on this, the amount of proteins on the immunoblots was quantified using National Institutes of Health (NIH) imaging software.

FIG. 1 shows HSP70 time-dependent induction (density of HSP70 relative to a baseline (BL)) following oral administration of GGA (200 mg/kg) or the vehicle and after heat stress (HS). As shown in FIG. 1, HSP70 was detected in the GGA group beginning about 6 hours after administration, and the amount detected (amount induced) peaked after 24 hours. After 48 hours, the detected amount had decreased. In the control group, no changes over time were, observed in the detected level of HSP70. From these results, it appears that oral administration of GGA induces HSP70 in the hearts of rats.

Figure 2:
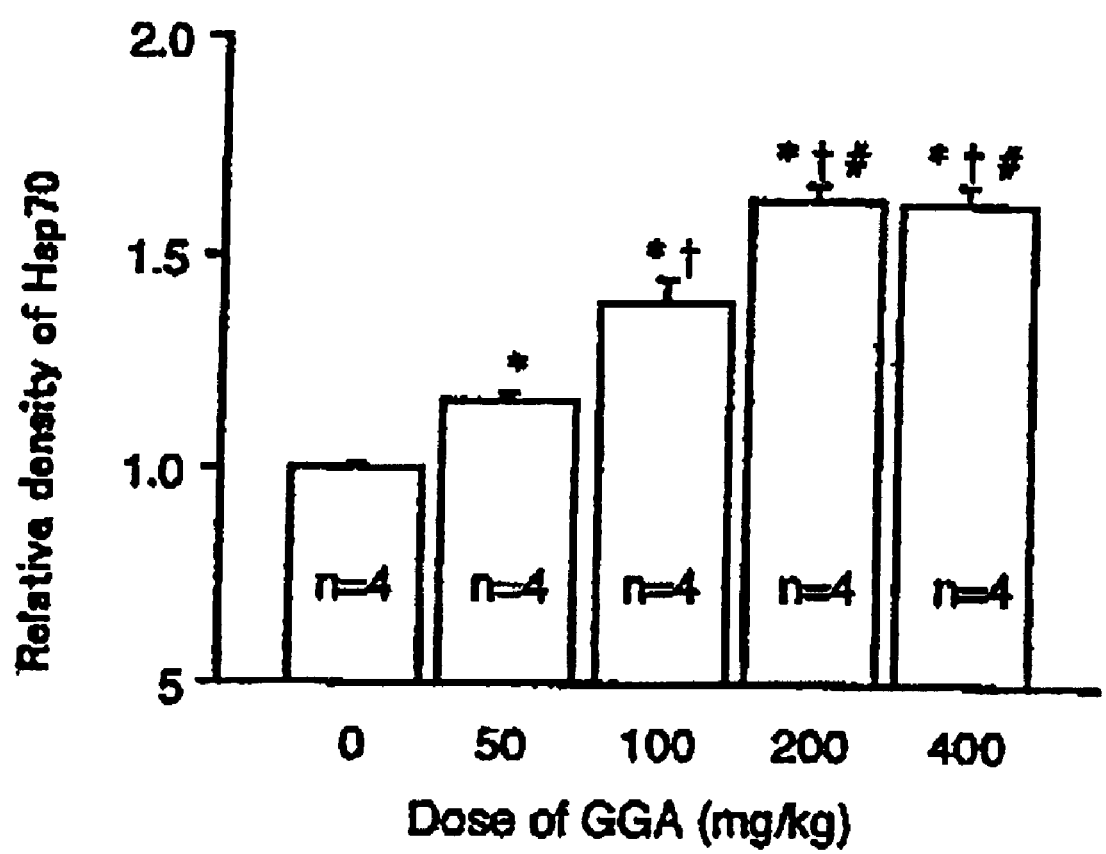
FIG. 2 is a graph showing measurement results for HSP70 induction in the heart following oral administration of different doses of GGA.

FIG. 2 shows measurement results for HSP70 induction (relative density of HSP70 compared with 0 mg/kg administration) in the heart following oral administration of different GGA dosages (0 mg/kg, 50 mg/kg, 100 mg/kg, 200 mg/kg, 400 mg/kg). The results in FIG. 2 are measurements of hearts removed from the rats 24 hours after oral administration. As shown in FIG. 2, the detected amount (induced amount) of HSP70 increased as the dosage increased, peaking at 200 mg/kg. No increase in detected amount was seen above 400 mg/kg.

FIG. 3 shows the measurement results for induction of HSP27 and HSP60 (relative density of HSP27 and HSP60 compared with the Control Group) following oral administration of GGA (200 mg/kg) or the vehicle. The results in FIG. 3 are measurements of hearts removed from the rats 24 hours after oral administration. As shown in FIG. 3(A), there was no obvious difference in HSP27 expression 24 hours after oral administration depending on whether GGA or the vehicle was administered. As shown in FIG. 3(B), the expression of HSP60 was significantly decreased in the GGA group compared with the control group.

FIG. 4 shows measurement results for induction of NOS and thioredoxin (relative density of eNOS and thioredoxin compared to the control group) in the hearts after oral administration of GGA (200 mg/kg) or the vehicle. The results in FIG. 4 are measurements of hearts removed from the rats 24 hours after oral administration. As shown in FIG. 4(A), neither iNOS nor eNOS was induced by administration of either GGA or the vehicle. As shown in FIG. 4(B), thioredoxin was not induced by administration of either GGA or the vehicle.

From these results, it appears that GGA administration induces HSP70 in the heart but does not induce HSP27, HSP60, NOS or thioredoxin in the heart.

Isolated Perfused Heart Experiments

As mentioned above, 24 hours after administration of 200 mg/kg of GGA or the vehicle, rats were heparinized (500 IU/kg, i.p.) and anesthetized with pentobarbital (50 mg/kg, i.p.).

Each heart was isolated and reperfused using the Langendorff method with Krebs-Henseleit buffer (pH 7.4, [in mM] 118 NaCl, 4.7 KCl, 2.5 $CaCl_2$, 1.2 $MgSO_4$, 1.2 $KH_2PO_4$, 25.0 $Na_2HCO_3$, 11.0 glucose) equilibrated with a 95% $O_2$, 5% $CO_2$ gas mixture at 36.5° C., 75 mmHg ($1.0 \times 10^4$ Pa).

A water-filled latex balloon was inserted through the mitral orifice into the left ventricle, and the left ventricular end diastolic pressure (LVEDP) was adjusted to 0–5 mmHg (0–667 Pa). During the first 10 minutes of constant pressure reperfusion, the perfusion flow rate was determined for each heart, and the hearts were then perfused at a determined perfusion rate using a microtube pump, during which time each heart was covered with water-jacketed glassware and humidity was maintained at 90% or more.

Normothermic no-flow global ischemia was performed for 20, 40 and 60 minutes, followed by reperfusion for 30 minutes. The coronary effluent from the 30-minute reperfusion period was collected for measurement of released creatine kinase (CK). The ratio of released CK to heart weight was analyzed by unpaired t-test.

The peak position and negative first derivaties of left ventricular pressure (dP/dt max and dP/dt min) were monitored using a pressure transducer. Left ventricular developed pressure (LVDP) was defined as the difference between left ventricular systolic and diastolic pressure. Coronary perfusion pressure (CPP) was calculated as the hydraulic pressure measured at the level of aortic cannulation. Changes in LVDP, CPP and dP/dt were analyzed by two-way analysis of variance (ANOVA), followed by the Bonferroni/Dunn test.

The LVDP, CPP and electrocardiogram were continuously recorded on a polygraph recorder (WS-681G, Nihon Koden, Tokyo), and stored on a PCM data recorder (RD-111T, TEAC, Tokyo) for later analysis.

Relative protein densities were compared using Mann-Whitney's U-test.

Figure 5:
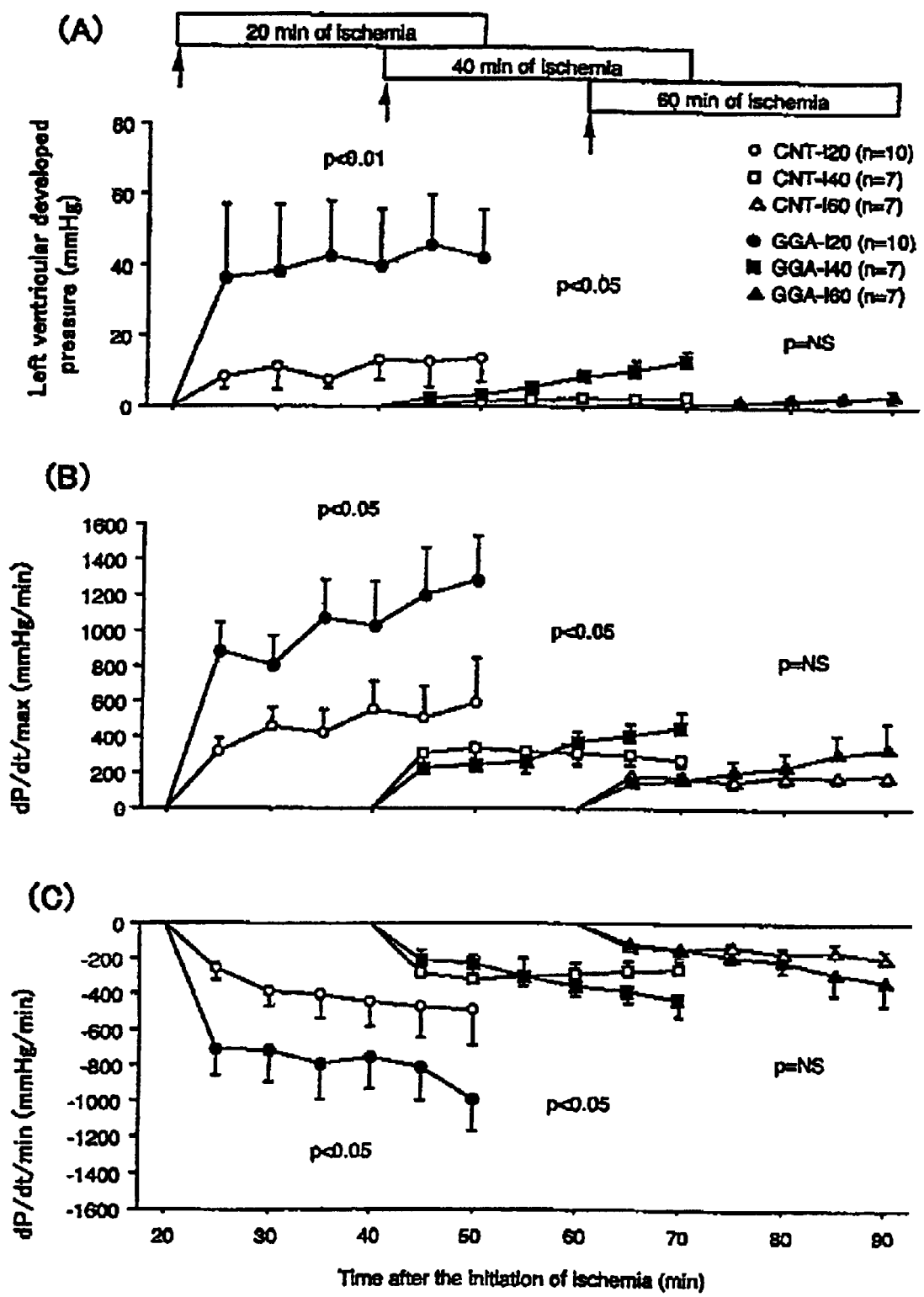
FIG. 5 is a graph showing (A) changes over time in LVDP, (B) changes over time in maximum dP/dt values and (C) changes over time in minimum dP/dt values during reperfusion.

Changes over time in LVDP and dP/dt during reperfusion are shown in FIG. 5. LVDP, dP/dt and other blood flow parameters at the baseline are shown in Table 1.

TABLE 1

| Parameter | Control group (n = 24) | GGA group (n = 24) |
|---|---|---|
| LVDP (mmHg) | 101.4 ± 3.8 | 103.0 ± 3.2 |
| Heart rate (beat/min) | 322.5 ± 9.8 | 318.0 ± 7.2 |
| CPP (mmHg) | 74.2 ± 1.8 | 73.4 ± 1.6 |
| DP/dt max (mmHg/min) | 3292.1 ± 151.2 | 3416.3 ± 139.5 |
| Dp/dt min (mmHg/min) | −2786.1 ± 135.3 | −2815.1 ± 132.5 |

Data are expressed as means ± SEM. GGA, geranylgeranylacetone; LVDP, left ventricular developed pressure; CPP, coronary perfusion pressure.

As shown in Table 1, there were no differences in the data at the baseline period between the GGA and Control Groups. During no-flow global ischemia, LVDP and dP/dt decreased rapidly to 0.

Subsequently, as shown in FIG. 5, maximum LVDP and dP/dt values increased as a result of reperfusion, while the minimum dP/dt value decreased. After about 20–40 minutes of reperfusion, the LVDP and dP/dt of the GGA Group were remarkably better than those of the Control Group. After about 60 minutes of reperfusion, functional recovery was poor in both groups, and no great difference was observed between the two. There was, however, no great difference between the two groups in CPP or heart rate depending on the reperfusion time (no graph).

The amount of creatine kinase (CK) released during reperfusion is shown in FIG. 6. As shown in FIG. 6, the amount of CK released was much less in the GGA Group than in the Control Group when the ischemic period was 20 or 40 minutes. There was no great difference between the groups when the ischemic period was 60 minutes.

Electron Microscope Findings

After 30 minutes of reperfusion followed by 20 minutes of no-flow ischemia, the papillary muscle of the left ventricle was immediately removed from the GGA-treated and Control hearts, and cut into small blocks. The tissue blocks were then fixed in a cacodylate buffered (pH 7.4) solution containing 2.5% glutaraldehyde and paraformaldehyde at 4° C. for 2 hours, and postfixed in a cocodylate buffered (pH 7.4) solution containing 2% osmium tetroxide and 0.5% potassium ferrocyanide at 4° C. for 2 hours. The tissue blocks were then dehydrated in ethanol and embedded in epoxy resin. Ultra-thin sections were stained with uranyl acetate and lead cistate, and were viewed under a transmission electron microscope (JOEL-100CX, Tokyo).

Observation of the myocardial cells by transmission electron microscopy revealed atrophic nuclei, swollen mitochondria and irregularly-arranged myofibrils in most of the myocardial cells of the control rats. The cristae of the mitochondria were destroyed. In addition, the intracellular spaces were enlarged. In contrast, the myocardial cells of the GGA-treated rats were preserved microstructurally, although some cells were slightly damaged. The nuclei were generally oval in shape, having densely packed chromatin disposed around the periphery of the nucleus. The myofibrils were arranged regularly and Z bands were clearly indentifiable. Although a few swollen mitochondria were observed, most of the sarcolemmal, interfibrillar and perinuclear mitochondria possessed well-developed cristae. The t-tubules were slightly expanded.

The heat shock protein inducer of the present invention was shown to have the effect of inducing heat shock proteins in the heart and improving cardiac function in an ischemic disease model using rat hearts.

Consequently, the heat shock protein inducer of the present invention is useful in the prevention or treatment of ischemic disease or ischemia/reperfusion injury in humans and other mammals.

Example 2

Materials

Monoclonal IgG cross-reactive to inducible HSP70 antibody was purchased from Stressgen Biotechnologies Corp. Monoclonal antibodies to PKC-α, -β, -γ, -δ and -ε were purchased from Transduction Laboratories. Horseradish peroxidase-linked F(ab')$_2$ fragment from sheep anti-mouse immunoglobulin and reagents for Western blot detection by enhanced chemiluminescence (ECL) were purchased from Amersham Pharmacia. Bradford protein assay kits were purchased from Bio-Rad Laboratories. GGA was provided by Eisai Co Ltd.

Animals

Figure 7:
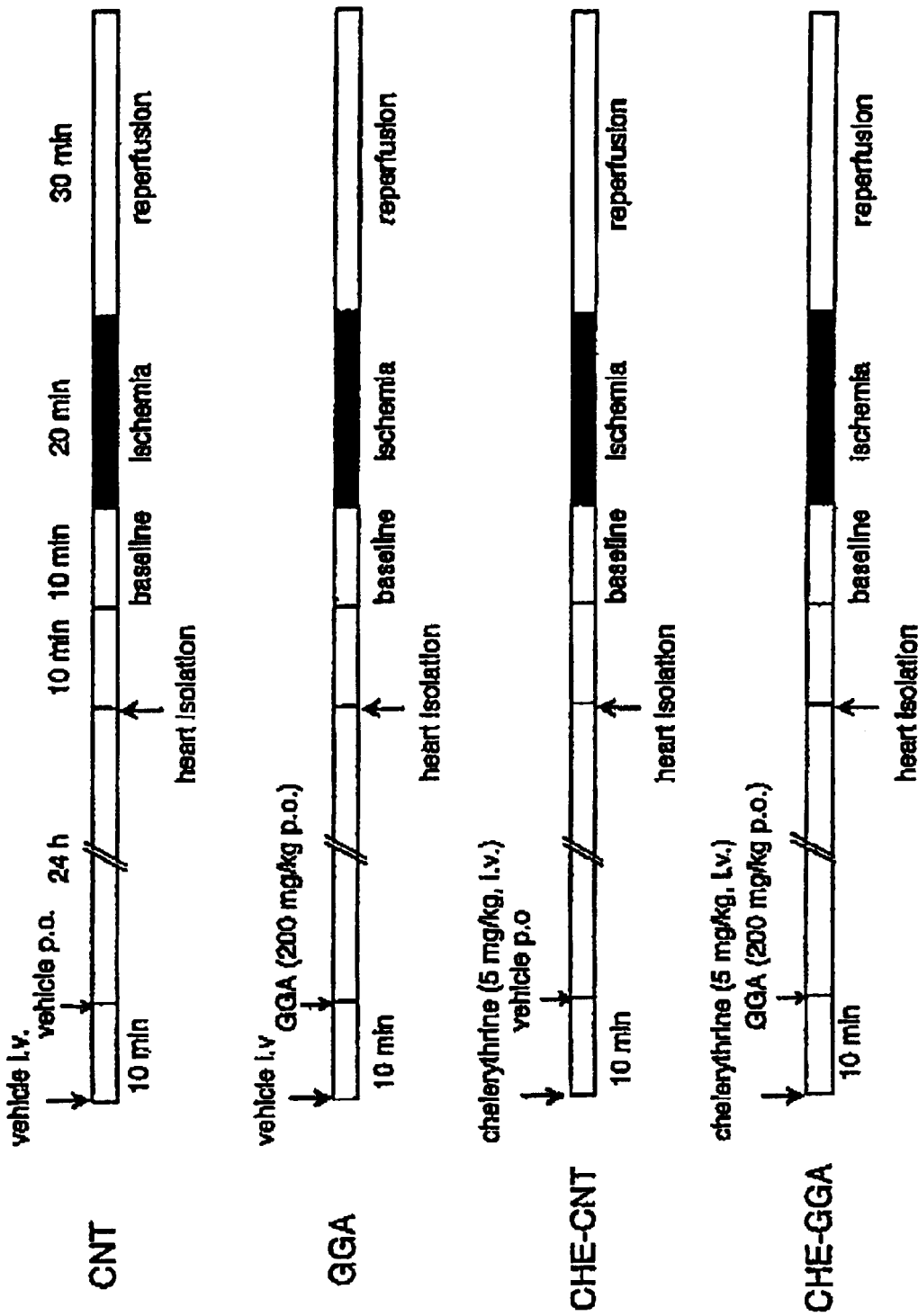
FIG. 7 is a diagrammatic representation showing the experimental protocol.

Male Sprague-Dawley rats (220–250 g) were used. GGA, as an emulsion with 5% gum arabic and 0.008% tocopherol, was given orally at a dose of 200 mg/kg. Rats were classified into 4 groups. FIG. 7 is a diagrammatic representation of experimental protocol. As shown in FIG. 7, 4 groups comprise a control (CNT) group (vehicle administration), a GGA group (GGA 200 mg/kg administration), a CHE-CNT group (pretreated with intravenous injection of 5 mg/kg cheleryth-rine before vehicle administration), and a CHE-GGA group (pretreated with chelerythrine before GGA administration). Twenty-four hours after oral administration of GGA or vehicle, rats were anesthetized (sodium pentobarbital, 50 mg/kg IP) and heparinized (500 IU/kg IP). Hearts were excised, immediately frozen in liquid nitrogen, and stored at −70° C. until use for Western blot analysis (n=4 for each group). To examine the cardiac function during ischemia and reperfusion, hearts of each group were prepared for isolated perfused experiments using Langendorff apparatus (n=7-9 for each group, FIG. 7).

Western Immunoblotting

To analyze the expression of HSP70, the frozen heart samples were homogenized with SDS sample buffer (pH 6.8, 20% glycerol, 6% SDS, 0.12M Tris), centrifuged and boiled (Maloyan A, Palmon A, Horowitz M. Heat acclimation increases the basal HSP70 level and alters its production dynamics during heat stress. Am J Physiol. 1999; 276:R1506–R1515.). For analysis of HSF1 in cytozolic and nuclear fraction, the frozen heart samples were homogenized in buffer A (pH 7.9, [in mM] 10 HEPES, 10 KCl, 0.1 EDTA, 0.1 EGTA, 1 DTT, 0.5 PMSF) containing 10% nonidet P-40, and centrifuged at 16,000 g for 30 s at 4° C. The supernatant was used as cytosolic fraction. The pellet was resuspended with buffer B (pH 7.9, [in mM] 20 HEPES, 400 NaCl, 20% glycerol, 1.5 MgCl$_2$, 1 EDTA, 1 EGTA, 1 DTT, 1 PMSF, 1 µg/ml leupeptin, 1 µg/ml aprotinin ) and incubated on ice for 15 min and centrifuged at 16,000 g for 5 min at 4° C. The supernatant thus obtained was used as nuclear fraction (Xu Q, Hu Y, Kleindienst R, et al. Nitric oxide induces heat-shock protein 70 expression in vascular smooth muscle cells via activation of heat shock factor 1. J Clin Invest. 1997;100:1089–1097). For analysis translocation of PKC, the ventricles were homogenized in homogenization buffer (pH 7.4, [in mM] 320 sucrose, 10 Tris HCl, 1 EGTA, 5 NaN$_3$, 10 β-mercaptoethanol, 0.02 leupeptin, 0.00015 pepstatin A, 0.2 phenylmethylsulfonyl fluoride, and 50 NaF). Homogenates were centrifuged at 1,000 g for 10 min at 4° C. The supernatant was designated as cytosolic fraction. The pellet was resuspended in homogenization buffer with 0.3% Triton X-100 and incubated on ice for 2 hours and centrifuged at 100,000 g for 1 hour. The supernatant was designated as particulate fraction (Yoshida K, Hirata T, Akita Y, et al. Translocation of protein kinase C-α, δ and ε isoforms in ischemic rat heart. Biochim Biophys Acta. 1996;1317:36–44). Western blotting was performed as previously described. The frozen heart preparations were homogenized with SDS sample buffer, centrifuged and boiled. The total protein concentration of heart was quantified by the Bradford method (Bradford MM. A rapid and sensitive method for quantitation of microgram quantities of protein utilizing the principle of protein-dye binding. Anal. Biochem. 1976;72:248–254). The preparations were diluted in dissociation buffer. An equal amount of total protein in each fraction was conducted on 8.5% SDS-PAGE, and transferred electrophoretically to a PVDF membrane. After transferring and blocking with 0.5% non-fat milk, the membranes were incubated with antibodies. The proteins were detected by ECL with exposure to Hyperfilm (Amersham Pharmacia). The amount of protein on the immunoblots was quantified using National Institutes of Health image software.

Effects of Chelerythrine (CHE) Pretreatment on GGA-Induced HSP70 Expression

Figure 8:
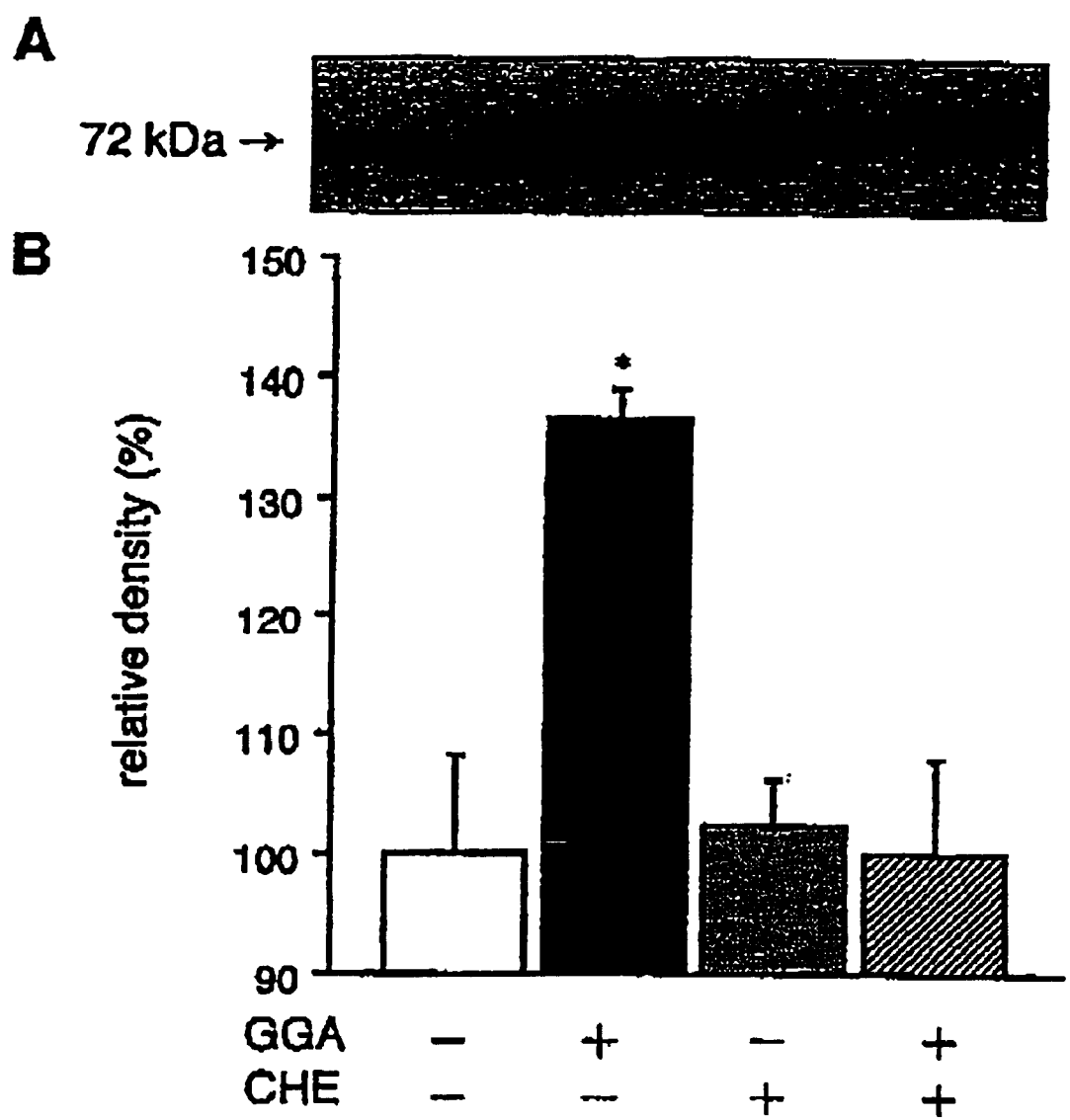
FIG. 8 is a graph showing effects of chelerythrine (CHE) pretreatment on geranylgeranylacetone (GGA)-induced heat shock protein 70 (HSP70) expression.

FIG. 8 shows effects of CHE pretreatment on GGA-induced HSP70 expression. Hearts were isolated 24 h after administration of GGA (200 mg/kg) or vehicle. (A) Representative expression of HSP70 in 4 groups. (B) Quantitative expression of HSP70. Data are relative density to that of control group. Data are mean ±SEM. *$p<0.05$ vs. control group. As shown in FIG. 8, the HSP70 expression was increased in GGA group compared to CNT group ($p<0.05$). Pretreatment with chelerythrine(PKC inhibitor) per se did not influence the expression of HSP70. However, the pretreatment with chelerythrine before GGA administration suppressed the GGA-induced HSP70 expression and GGA-induced HSF1 phosphorylation and its translocation from the cytosol to the nucleus, resulting in no significant difference among CNT, CHE-CNT, and CHE-GGA groups.

Effects of Chelerythrine Pretreatment on GGA-Induced HSF1 Phosphorylation

Figure 9:
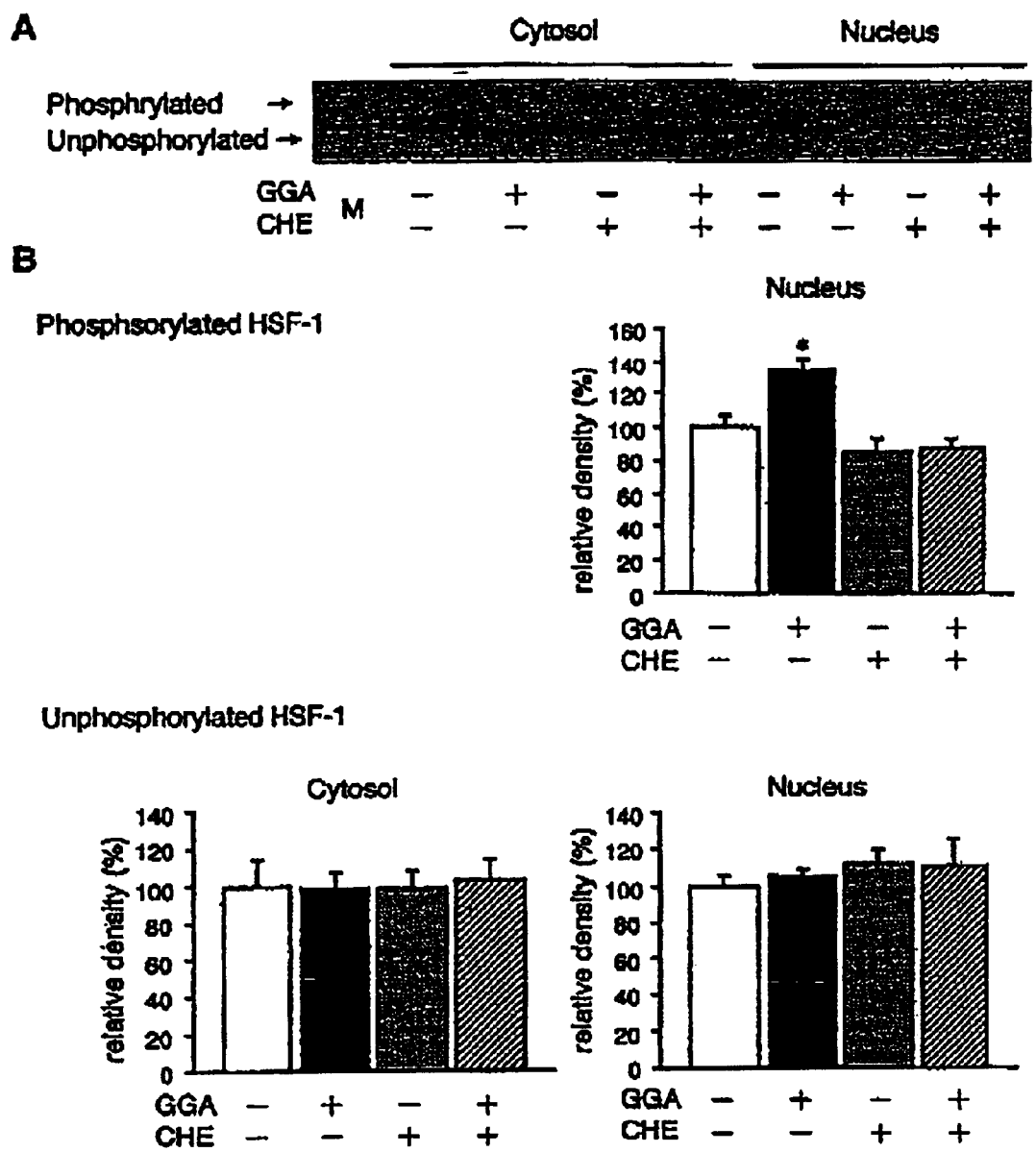
FIG. 9 is a graph showing effects of chelerythrine (CHE) pretreatment on geranylgeranylacetone (GGA)-induced heat shock factor 1 (HSF1) phosphorylation and its translocation. (A) Representative expression of phosphorylated and unphosphorylated forms of HSF1 in cytosolic and nuclear fractions in the 4 groups. (B) Quantitative expression of phosphorylated and unphosphorylated forms of HSF1.

FIG. 9 shows effects of chelerythrine (CHE) pretreatment on geranylgeranylacetone (GGA)-induced heat shock factor 1 (HSF1) phosphorylation and its translocation. (A) Representative expression of phosphorylated and unphosphorylated forms of HSF1 in cytosolic and nuclear fractions in the 4 groups. (B) Quantitative expression of phosphorylated and unphosphorylated forms of HSF1. Data are relative density to that of control group. Data are mean ±SEM. *$p<0.05$ vs. control group. M, positive marker. As shown in FIG. 9, in cytosolic fraction, only one band representing the unphosphorylated form of HSF1 was observed in all the 4 groups without any significant differences in its amount. In the nuclear fraction, another band representing the phosphorylated form of HSF1 was also detectable. The amount of phosphorylated form of HSF1 in the nuclear fraction was increased in the GGA group compared to the CNT group ($p<0.05$). Pretreatment with chelerythrine before GGA administration suppressed the increase of nuclear phosphorylated form of HSF1 while the chelerythrine per se did not significantly influence the amount of two forms of HSF1.

Figure 10:
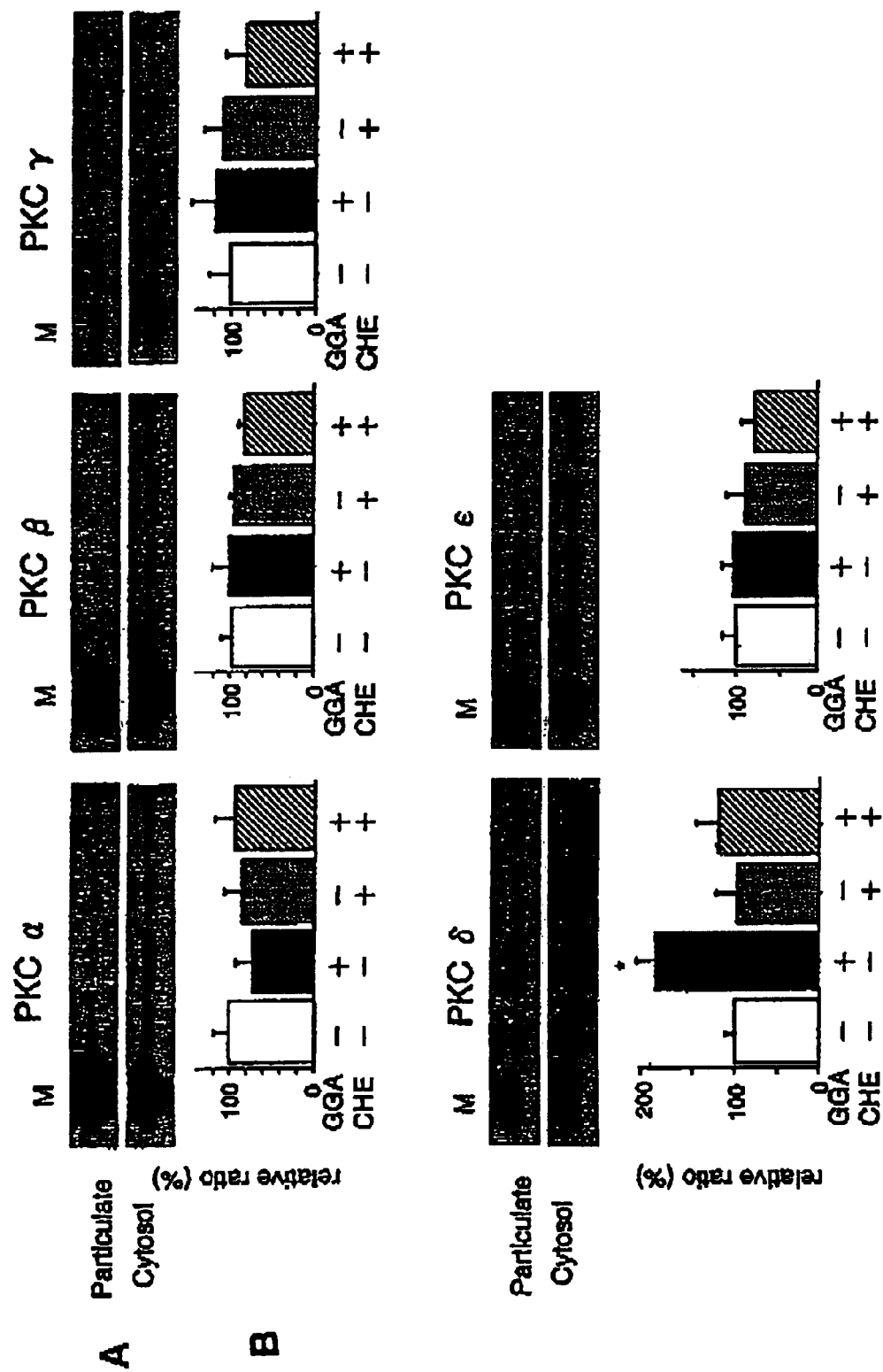
FIG. 10 is a graph showing effects of chelerythrine (CHE) pretreatment on geranylgeranylacetone (GGA)-induced translocation of protein kinase C (PKC) isoforms. (A) Representative expression of PKCα, β, γ, δ and ε in particulate and cytosolic fractions in the 4 groups. (B) Quantitative expression of PKCα, β, γ, δ and ε.

Effects of Chelerythrine Pretreatment on GGA-Induced Translocation of PKC Isoforms FIG. 10 shows effects of chelerythrine (CHE) pretreatment on geranylgeranylacetone (GGA)-induced translocation of protein kinase C (PKC) isoforms. (A) Representative expression of PKCα, β, γ, δ and ε in particulate and cytosolic fractions in the 4 groups. (B) Quantitative expression of PKCα, β, γ, δ and ε. The particulate/cytosol ratio was calculated and expressed as relative ratio to that of control group as. Data are mean ±SEM. *$p<0.05$ vs. control group. M, positive marker. As depicted in FIG. 10, in the heart of control rats, all the isoforms of PKC examined were detectable both in particulate and cytosolic fractions. In the GGA group, the PKCδ isoform in the particulate fraction was increased, resulting in the significant increase in a particulate/cytosol fraction ratio compared to the CNT group ($p<0.05$). Pretreatment with chelerythrine per se did not influence the PKCδ in both particulate and cytosolic fractions. However, the pretreatment with chelerythrine partially but significantly suppressed the GGA-induced increase of PKCδ in the particulate fraction. Therefore, the particulate/cytosol ratio of PKCδ was not significantly different among the CNT, CHE-CNT, and CHE-GGA groups. Another 4 isoforms of PKC (α, β, γ and ε) in both the cytosolic and particulate fractions were not influenced by administration of GGA, pretreatment with chelerythrine or both among all the 4 groups. In a GGA-induced HSP70 overexpressed heart, a translocation of PKCδ from cytosol to particulate was observed, which was also prevented by the pretreatment with chelerythrine. This finding suggests that PKCδ isoform plays a key role for HSF1 activation.

Isolated Perfused Heart Experiments

Twenty-four hours after administration-of 200 mg/kg of GGA or vehicle, rats of 4 groups were heparinized (500 IU/kg, IP) and anesthetized with sodium pentobarbital (50 mg/kg, IP). Each heart was isolated and perfused retrogradely using the Langendorff method with Krebs-Henseleit buffer (pH 7.4, [in mM] 118 NaCl, 4.7 KCl, 2.5 $CaCl_2$, 1.2 $MgSO_4$, 1.2 $KH_2PO_4$, 25.0 $Na_2HCO_3$, 11.0 glucose) equilibrated with 95% $O_2$–5% $CO_2$ gas mixture at 36.5° C. at a constant pressure of 75 mm Hg. A water-filled latex balloon was inserted through the mitral orifice into the left ventricle (LV) and the LV end-diastolic pressure (LVEDP) was adjusted to 0–5 mm Hg. During the initial 10 min of constant pressure perfusion, the perfusion flow rate was determined for each heart, which was then perfused at a determined perfusion rate using a microtube pump while the heart was covered with water-jacketed glassware and the relative humidity maintained at 90% or more. Normothermic no-flow global ischemia was initiated for 20 min, followed by reperfusion for 30 min. The coronary effluent during the 30 min of reperfusion period was collected for measurement of creatine kinase content (released CK).

LV pressure was monitored using a pressure transducer to obtain the peak positive and negative first derivatives of LV pressure ($dP/dt_{max}$ and $dP/dt_{min}$). LV developed pressure (LVDP) was defined as the difference between the LV systolic and diastolic pressure. Coronary perfusion pressure (CPP) was defined as the hydraulic pressure measured at the level of aortic cannulation. LV pressure, CPP and electrocardiogram were continuously recorded on a polygraph recorder (WS-681G, Nihon Kohden) and stored on a PCM data recorder (RD-111T, TEAC) for later analysis.

Statistical Analysis

Data are expressed as mean ±SEM. Serial changes in LVDP, LVEDP, CPP, and dP/dt were analyzed by two-way analysis of variance (ANOVA) followed by the Bonferroni/Dunn test, unless otherwise specified. Comparisons among groups with respect to the hemodynamic parameters at baseline and the ratio of released CK to ventricular weight were analyzed by one-way ANOVA followed by the Bonferroni/Dunn test. The relative intensity of each protein was compared using Mann-Whitney's U-test. A value of $p<0.05$ was considered significant.

Isolated Perfused Heart Experiments

TABLE 2

| | CNT group (n = 9) | GGA group (n = 9) | CHE-CNT group (n = 7) | CHE-GGA group (n = 7) |
|---|---|---|---|---|
| LVDP (mmHg) | 96.3 ± 9.8 | 100.6 ± 9.7 | 95.3 ± 5.1 | 91.7 ± 10.8 |
| Heart rate (beat/min) | 341.0 ± 14.0 | 331.0 ± 35.9 | 352.7 ± 10.8 | 347.2 ± 19.9 |
| CPP (mmHg) | 77.8 ± 1.9 | 74.2 ± 1.3 | 82.1 ± 2.9 | 73.3 ± 1.7 |
| DP/dt max (mmHg/min) | 3637.5 ± 452.4 | 3865.5 ± 288.1 | 3631.6 ± 163.1 | 3170.6 ± 215.0 |
| Dp/dt min (mmHg/min) | −2724.4 ± 247.5 | −3533.9 ± 254.3 | −2086.2 ± 64.5 | −2150.3 ± 373.8 |

Data are expressed as means ± SEM. LVDP, left ventricular developed pressure; CPP, coronary perfusion pressure.

As shown in Table 2, none of LVDP, heart rate, CPP or dP/dt differed among the 4 groups at baseline period.

Figure 11:
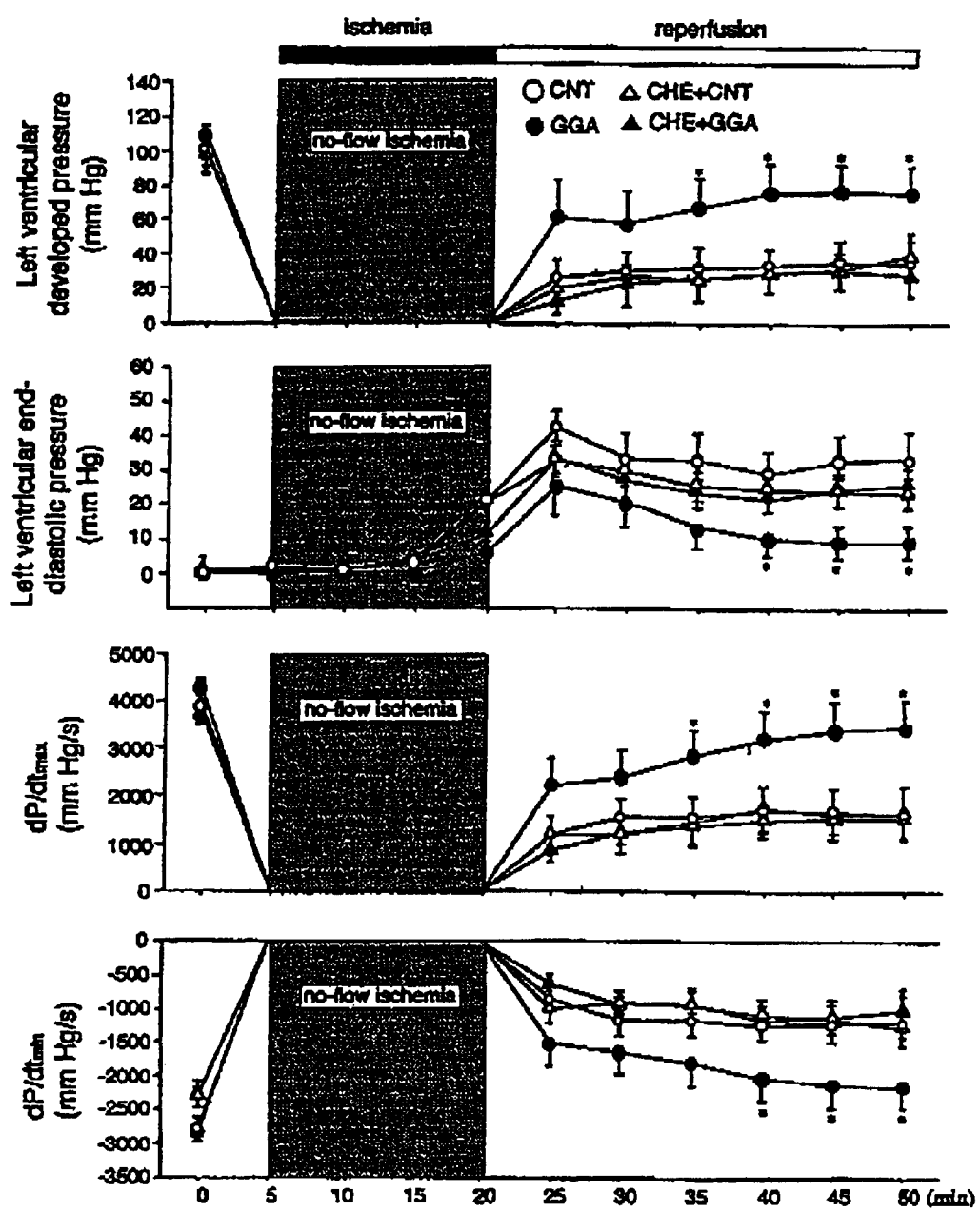
FIG. 11 is a graph showing serial changes of left ventricular developed pressure, left ventricular end-diastolic pressure, dP/dt max and dP/dt min during the experimental period in the 4 groups.

FIG. 11 shows serial changes of left ventricular developed pressure, left ventricular end-diastolic pressure, dP/dt max and dP/dt min during the experimental period in the 4 groups. Thirty minutes of reperfusion was followed by 20 min of no-flow global ischemia. Data are mean ±SEM in each group. FIG. 11 exhibits the serial changes LVDP, LVEDP and dP/dt during the experimental period. On reperfusion, the LVDP and $dP/dt_{max}$ increased and $dP/dt_{min}$ decreased. The LVEDP showed transient increase followed by gradual decrease. The recovery of LVDP, LVEDP and dP/dt was greater in GGA group than in the CNT group (p<0.05 for each by ANOVA). The recovery of these parameters in the CHE-CNT group was similar to that in the CNT group. The pretreatment with chelerythrine before GGA administration (CHE-GGA group) abolished better functional recovery observed in the GGA group. Thus, the recovery of LVDP, LVEDP and dP/dt in CNT group and CHE-CNT group was not significantly different from those of CHE-GGA group. CPP and heart rate did not differ significantly at any periods among the 4 groups (data not shown). These results suggest that an activation of PKC priming the phosphorylation of HSF1 may play an essential role for the cardiac overexpression of HSP70 by GGA, leading to cardioprotection.

FIG. 12 shows the amount of released creatine kinase (CK) relative to ventricular weight during the 30-min reperfusion period. Data are mean ±SEM. *p<0.05 vs. control group. As shown in FIG. 12, the released CK was lower in the GGA group compared with the CNT group (p<0.05). The value in the CHE-CNT group was similar to that in CNT group. The pretreatment with chelerythrine before GGA administration (CHE-GGA group) abolished the reduction in the value observed in the GGA group, resulting in no significant differences between the CHE-GGA and CHE-CNT groups. These results suggest that activation of PKC plays an essential role for priming the GGA-induced HSF1 activation. PKC may mediate the GGA-induced posphorylation of HSF1, resulting in promoting the HSP70 expression. Abolishment of the better functional recovery induced by GGA by the pretreatment with chelerythrine also suggest that HSP70 induced by GGA plays an essential role for cardioprotection against ischemia/reperfusion injury.

Aforesaid EXAMPLE2 shows that oral GGA would activate protein kinase C (PKC), leading to the phosphorylation and translocation of the heat shock factor 1(HSF1), and thus promote the expression of HSP70, leading to cardioprotection against ischemia/reperfusion injury.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of preventing or treating ischemic disease comprising administering a heat shock protein inducer to a patient in need thereof.

2. A method of preventing or treating ischemia/reperfusion injury comprising administering a heat shock protein inducer to a patient in need thereof.

3. The method of claim 1 or 2 wherein the heat shock protein inducer is administered orally.

4. The method of claim 1, wherein the heat shock protein inducer is geranylgeranylacetone.

5. The method of claim 2, wherein the heat shock protein inducer is geranylgeranylacetone.

6. The method of claim 3, wherein the heat shock protein inducer is geranylgeranylacetone.

* * * * *

UNITED STATES PATENT AND TRADEMARK OFFICE
CERTIFICATE OF CORRECTION

PATENT NO.    : 6,846,845 B2
DATED         : January 25, 2005
INVENTOR(S)   : Takahashi et al.

It is certified that error appears in the above-identified patent and that said Letters Patent is hereby corrected as shown below:

Column 6,
Line 35, before "Examples", insert new paragraph:

-- Accordingly, the invention is directed to a heat shock protein inducer having geranylgeranylacetone as an active ingredient and which induces heat shock proteins in a heart. The heat shock protein can be HSP70. The invention is also directed to a method of preventing or treating ischemic disease, the method comprising the administration of a heat shock protein inducer having geranylgeranylacetone as an active ingredient and which induces heat shock proteins in a heart to a patient in need thereof. The invention is also directed to a method of preventing or treating ischemic/reperfusion injury, the method comprising the administration of a heat shock protein inducer having geranylgeranylacetone as an active ingredient and which induces heat shock proteins in a heart to a patient in need thereof. In either method, the heat shock protein inducer can be administered orally. Further the invention is directed to a medicament having geranylgeranylacetone as its active ingredient which is used for preventing or treating ischemic disease or ischemia/reperfusion injury; this medicament can be an oral medicament. --

Column 14,
Lines 40-43, please delete claim 1, "A method of preventing or treating ischemic disease comprising administering a heat shock protein inducer to a patient in need thereof", and replace it with the following claim:
-- A method for inducing heat shock protein in a heart of a patient in need thereof, said method comprising administering to said patient, a composition consisting essentially of geranylgeranylacetone in an amount effective to induce heat shock protein HSP70 in said heart of said patient. --.
Lines 44-46, please delete claim 2, "A method of preventing or treating ischemia/ reperfusion injury comprising administering a heat shock protein inducer to a patient in need thereof", and replace it with the following claim:
-- A method for enhancing expression of heat shock protein in heart cells of a patient in need thereof, said method comprising administering to said patient a composition consisting essentially of therapeutic dose of geranylgeranylacetone, said therapeutic dose being an amount effective to enhance expression of heat shock protein HSP70 in said heart cells. --.

UNITED STATES PATENT AND TRADEMARK OFFICE
CERTIFICATE OF CORRECTION

PATENT NO. : 6,846,845 B2
DATED : January 25, 2005
INVENTOR(S) : Takahashi et al.

It is certified that error appears in the above-identified patent and that said Letters Patent is hereby corrected as shown below:

Column 14 (cont'd),
Lines 47-54, please delete claims 3-6.

Signed and Sealed this

Twenty-seventh Day of September, 2005

JON W. DUDAS
*Director of the United States Patent and Trademark Office*